United States Patent [19]

Subramanian et al.

[11] 4,017,595
[45] Apr. 12, 1977

[54] BONE-SEEKING INDIUM-113M OR INDIUM-111 ORGANIC PHOSPHONATE COMPLEXES

[75] Inventors: Gopal Subramanian, Manlius; John Gilmour McAfee, Fayetteville, both of N.Y.

[73] Assignee: Research Corporation, New York, N.Y.

[22] Filed: Aug. 28, 1975

[21] Appl. No.: 608,695

[52] U.S. Cl. .................................. 424/1; 250/303; 260/429 R

[51] Int. Cl.² .................. A61K 29/00; A61K 43/00

[58] Field of Search .................. 260/502.5, 429 R; 424/1; 250/303; 128/2 A

[56] References Cited

OTHER PUBLICATIONS

Castronovo et al., Journal of Nuclear Medicine, vol. 13, No. 11, 1972, pp. 823–827.
O'Mara et al., Seminars in Nuclear Medicine, vol. 2, No. 1, Jan. 1972, pp. 38–49.
Hégésippe et al., Journal of Nuclear Biology and Medicine, vol. 17, No. 3, 1973, pp. 93–96.
Hosain et al., British Journal of Radiology, vol. 45, Sept. 1972, pp. 677–679.
Burdine, Jr. et al., Journal of Nuclear Medicine, vol. 10, No. 6, June 1969, pp. 290–293.
Merrick et al., Chemical Abstracts, vol. 82, No. 23, June 9, 1975, p. 226, abstract No. 151486g.
Sundberg et al., Chemical Abstracts, vol. 82, No. 7, Feb. 17, 1975, p. 42, abstract No. 38709u.

Primary Examiner—Benjamin R. Padgett
Assistant Examiner—Christine M. Nucker
Attorney, Agent, or Firm—Cameron, Kerkam, Sutton, Stowell & Stowell

[57] ABSTRACT

The invention relates to bone-seeking compositions suitable for use as skeletal imaging agents comprising complexes of Indium-113m or Indium-111 with various organic phosphonates, methods of preparation thereof, compositions for skeletal imaging and methods of skeletal imaging comprising the administration of these phosphonates.

14 Claims, 1 Drawing Figure

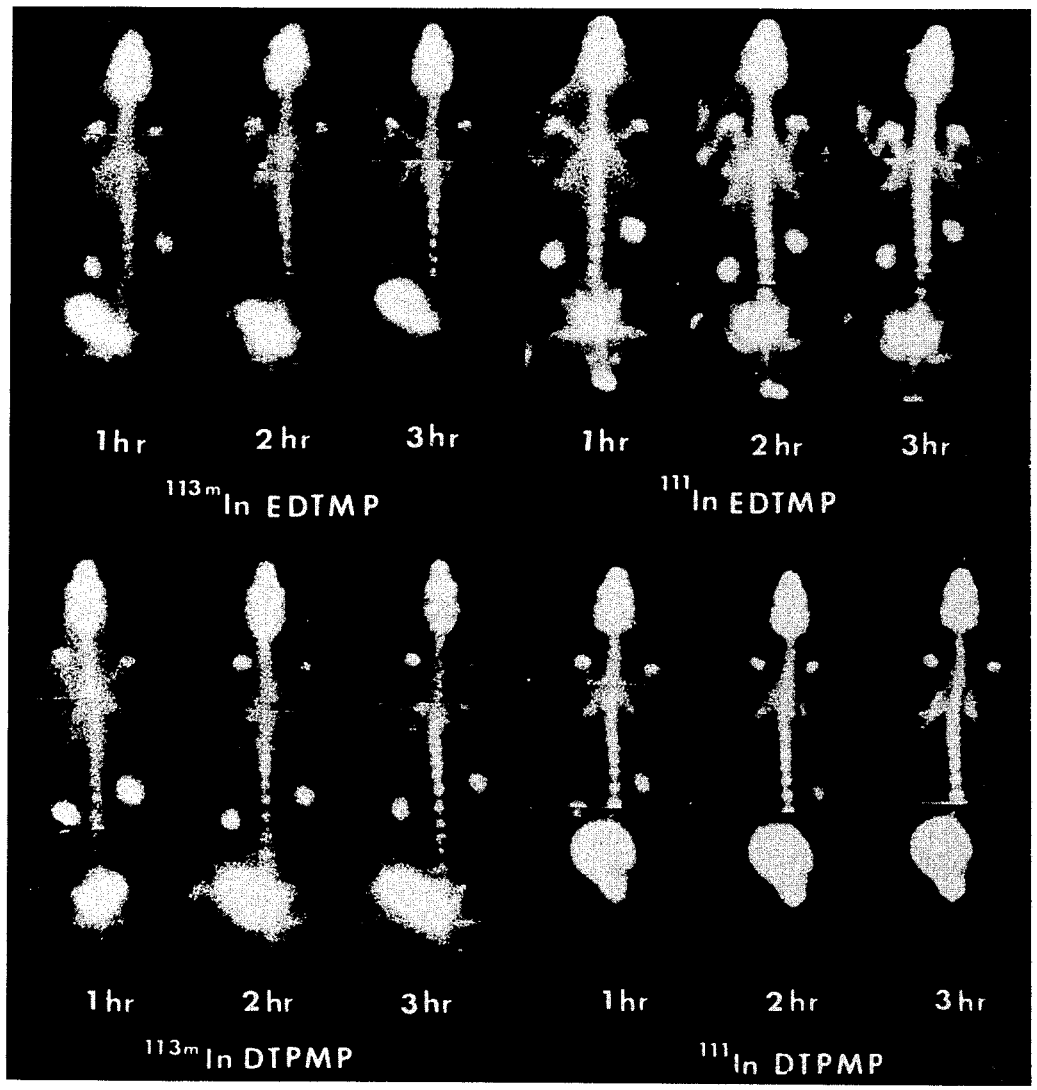

BONE-SEEKING INDIUM-113M OR INDIUM-111 ORGANIC PHOSPHONATE COMPLEXES

BACKGROUND OF THE INVENTION

Recently, various complexes of radionuclides have been proposed for the external imaging of various portions of the anatomy. Various compositions have been found to localize to a greater extent in certain organs than in others thereby enabling the imaging of that organ, utilizing a suitable radioactivity sensitive camera, etc.

Of the agents currently employed for skeletal imaging, the radionuclides Strontium 85 and Fluorine 18 have found widespread use. Fairly recently, complexes of Technetium-99m with various organic complexing agents have been found to be superior to the strontium 85 and fluorine 18 agents. Generally, the complexing agents employed are organic phosphate and phosphonate chelating agents. See Perez et al, *J. Nucl. Med.* 13:788–789, 1972; Subramanian et al, *Radiology*, 98: 192-196, 1971; Subramanian et al, *Radiology*, 102:701-704, 1972; Subramanian et al, *J. Nucl. Med.*, 13:947-950, 1972; Tofe et al, *J. Nucl. Med.*, 15:69–74, 1974; Yano, *J. Nucl. Med.*, 14:73-78, 1973; Castronova et al, *J. Nucl. Med.*, 13:823-827, 1972; and Subramanian et al, *J. Nucl. Med.*, August, 1975 (U.S. application Ser. No. 368,473, filed June 11, 1973).

It was found that when solutions of these Technetium-99m phosphate and phosphonate complexes are given intravenously, the Technetium-99m localizes to a great extent in bone, particularly in diseased or abnormal areas of the skeleton. Good visualization of both normal bone and skeleton lesions is observed about 2 hours after administration of the complexes. Normal and abnormal skeletal tissues are readily delineated using conventional radioisotope imaging devices such as rectilinear scanners or scintillation cameras.

There has been a continuing search in this area for other radionuclides and complexing agents with high bone uptakes suitable for skeletal imaging where Technetium 99m and/or the complexing agents utilized heretofore are not available.

SUMMARY OF THE INVENTION

It has been found that a complex of Indium-113m or Indium-111 with ethylene diamine tetra(methylene phosphonic) acid, diethylene triamine penta(methylene phosphonic) acid or a salt thereof with a pharmaceutically acceptable cation are highly effective skeletal imaging agents with high uptake in bone and good imaging properties.

The invention relates to a method for preparing these complexes by admixing in aqueous solution Indium-113m or Indium 111 ethylene diamine tetra(methylene phosphonic) acid or a salt thereof with a pharmaceutically acceptable cation.

The invention also relates to a bone-seeking composition comprising a solution adapted for intravenous administration containing one of the above indium complexes.

The invention also relates to a method of skeletal imaging which includes the intravenous administration of a solution adapted for intravenous administration containing one of the above indium complexes.

DETAILED DESCRIPTION OF THE INVENTION

Indium 113-m is a well-known short-lived radionuclide with excellent physical characteristics, including a monoenergetic gamma emission of 393 kev and a physical half-life of 100 minutes. The isotope is available as the daughter nuclide of its long-lived parent $^{113}$Sn. Generators for this nuclide are available (Subramanian et al, *Int. J. Appel. Radiat. Isotopes*, 18: 215–221, 1967 and Arino et al, *Int. J. Appel. Radiat. Isotopes*, 25: 493–496, 1974). This radionuclide has been previously employed in the nuclear medicine area for imaging most major organs in man with the exception of the skeleton. (Stern et al, *Nucleonics*, 24:57–61, 1966; Stern et al, *Nucleonics*, 25:62–66, 1967; Adatepe, et al, *J. Nucl. Med.* 9:426–427, 1968; Potchen et al, *JAMA* 205:208–214, 1968; O'Mara et al, *J. Nucl. Med.*, 10:18–27, 1969; and Cooper et al, Proceedings of a panel (IAEA PL 392/11) pp. 83–90, IAEA Vienna 1971).

The complexing agent, ethylene diamine tetra (methylene phosphonic) acid has the structural formula:

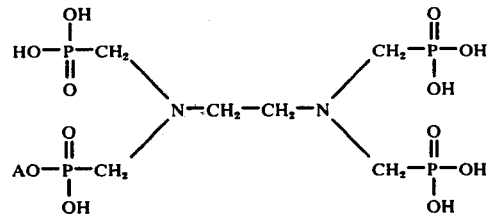

The complexing agent, diethylene triamine penta(methylene phosphonic)acid has the structural formula:

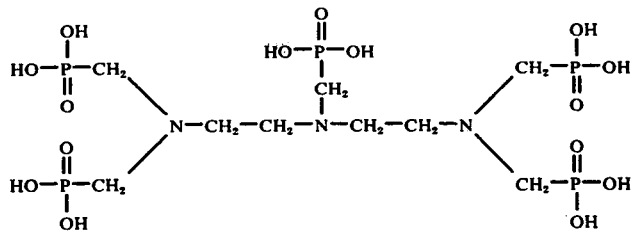

The bone-seeking compositions of the invention may be prepared from the free acids or salts thereof with pharmaceutically acceptable cations such as sodium, potassium, ammonium, etc.

The complexes of the invention are prepared by admixing in aqueous solution the required amount of either Indium-113m or Indium-111 with the appropriate amount of phosphonic acid or salt and adjusting the pH of the resulting solution to 7.0–8.0 either with dilute (0.1N) sodium hydroxide or dilute (0.1N) HCl as required since the phosphonic acid salt dissolved in water exhibits a high pH and the initial pH of the mixture will vary depending on the volume of the acidic indium solution employed.

The compositions of the invention are preferably employed in skeletal imaging applications in the form of the aqueous solutions produced according to the above method. The solutions may be prepared by the technician immediately prior to administration by admixing the required reagents in water, adjusting the pH and administering the solution intraveneously to the patient. Generally, the bone-seeking composition adapted for intravenous administration is provided in unit dosage form containing from about 5 to about 20 mCi of radioactivity. To prepare the composition, one simply admixes a sufficient amount of Indium-113m or Indium 111 having the required radioactivity with the complexing agent in a volume of water sufficient to provide an amount equivalent to the unit dosage. The unit dosage may contain from about 1 to about 5 ml. Generally, successful results can be obtained by administering from about 0.5 to about 0.5 mg of complex per kg of body weight, based on the weight of the free phosphonic acid complexing agent.

The indium isotopes employed in the following examples were obtained from sterile generators in 0.05 N HCl solutions and contained less than $10^{-4}$% Sn-113 and 5$\mu$g 1 ml of zirconia as impurities. No detectable gamma emitting impurities were present.

EXAMPLE 1

25 mg of ethylene diamine tetra(methylene phosphonic) acid and 8.5 mCi of Indium-113m were admixed in 8 ml of water. The pH was adjusted to 7.5–8.0 with dilute NaOH. The solution was sterilized by membrane filtration through a 0.22$\mu$ Millipore filter. The preparation was analyzed for free indium by gamma counting of paper electrophoresis strips and found to contain less than 2% free indium.

EXAMPLE 2

25 mg of diethylene triamine penta(methylene phosphonic) acid and 8.5 mCi of Indium-111 were admixed in 8 ml of water. The pH was adjusted to 7.5–8.0 with dilute NaOH. The solution was sterilized by membrane filtration through a 0.22$\mu$ Millipore filter. The preparation was analyzed for free indium according to the method of Example 1 and found to contain less than 2% free indium.

EXAMPLE 3

25 mg of ethylene diamine tetra(methylene phosphonic) acid and 5.0 mCi of Indium-111 were admixed in 6 ml of water. The pH was adjusted to 7.5–8.0 with dilute NaOH. The solution was sterilized by membrane filtration through a 0.22$\mu$ Millipore filter. The preparation was analyzed for free indium by gamma counting of paper electrophoresis strips and found to contain less than 2% free indium.

EXAMPLE 4

25 mg of diethylene triamine penta(methylene phosphonic) acid and 5.0 mCi of Indium-111m were admixed in 6 ml of water. The pH was adjusted to 7.5–8.0 with dilute NaOH. The solution was sterilized by membrane filtration through a 0.22$\mu$ Millipore filter. The preparation was analyzed for free indium by gamma counting of paper electrophoresis strips and found to contain less than 2% free indium.

EXAMPLE 5

This example illustrates an external imaging method employing the complexes of the invention. The complexes were prepared according to Examples 1–4.

3–5 mCi of each of the complexes of Examples 1–4 (containing 5–10 Mg of phosphonate) were injected intravenously into adult albino rabbits weighing 3.5–5 kgs. Imaging was performed 1–3 hours later in the posterior projection using a gamma camera (Searle Radiographics, HP, Des Plaines Ill.). A 410 kev parallel hole collimator was used for the Indium-113m complex and a 250 kev parallel hole collimator was used for the indium-111 complex. The whole body images of each rabbit were constructed from 3 separate images collecting 300 K counts each and are shown in the drawing. The images demonstrate the preferential localization of the complexes in the skeleton with considerable excretion of the radioactivity in the urine.

EXAMPLE 6

This example shows the organ distribution characteristics of ethylene diamine tetra(methylene phosphonic) acid (EDTMP) and diethylene triamine penta(methylene phosphonic) acid (DTPMP) complexes of Indium-113m.

0.5–1.0 mCi of the complexes prepared according to Examples 1 and 4 (containing 2–5 mg of the phosphonate complex) were injected intravenously into adult albino rabbits weighing 3.5–5 kg. Simultaneously, similar rabbits were injected intraveneously with 10–20$\mu$Ci of Strontium-85 as a biological standard for comparison. Organ distribution characteristics of these compositions were determined after sacrificing the animals 1–4 hours after injection using the method described in Perez et al, *J. Nucl. Med.* 13:788–789, 1972; Subramanian et al, *Radiology*, 98:192–196, 1971; Subramanian et al, *Radiology*, 102:701–704, 1972; Subramanian et al, *J. Nucl. Med.*, 13:947–950, 1972; Tofe et al, *J. Nucl. Med.*, 15:69–74, 1974; Yano, *J. Nucl Med.*, 14:73–78, 1973; Castronova et al, *J. Nucl. Med.*, 13:823–827, 1972; and Subramanian et al, *J. Nucl. Med.*, August, 1975 (U.S. application Ser. No. 368,473, filed June 11, 1973). Appropriate corrections were made for Strontium-85 contributions in the Indium-113m windows. The results are set forth in Table 1.

Table 1

| | Indium 113m labeled EDTMP and DTPMP in Rabbits Simultaneous Study with Strontium-85 | | | | | | | | | | | |
|---|---|---|---|---|---|---|---|---|---|---|---|---|
| | EDTMP: Ethylene diamine Tetra (Methylene Phosphonate) | | | | | | DTPMP: Diethylene Triamine Penta (Methylene phosphonate) | | | | | |
| | 1 Hr. | | 2 Hr. | | 4 Hr. | | 1 Hr. | | 2 Hr. | | 4 Hr. | |
| Organ | $^{113m}$In | $^{85}$Sr | $^{113m}$In | $^{85}$Sr | $^{113m}$In | $^{85}$Sr | $^{113m}$In | $^{85}$Sr | $^{113m}$In | $^{85}$Sr | $^{113m}$In | $^{85}$Sr |
| | % Dose in Whole Organ | | | | | | | | | | | |
| Blood | 12.6 | 10.6 | 8.49 | 6.58 | 4.88 | 4.12 | 8.61 | 11.9 | 3.88 | 6.66 | 3.08 | 5.06 |
| Liver | 1.57 | 1.60 | 0.769 | 1.05 | 0.483 | 0.593 | 0.702 | 1.69 | 0.453 | 1.02 | 0.354 | 0.675 |
| Muscle | 6.75 | 13.3 | 4.79 | 9.96 | 3.29 | 6.50 | 4.61 | 13.1 | 1.92 | 9.59 | 1.92 | 8.65 |

Table 1-continued

Indium 113m labeled EDTMP and DTPMP in Rabbits
Simultaneous Study with Strontium-85

| | EDTMP: Ethylene diamine Tetra (Methylene Phosphonate) | | | | | | DTPMP: Diethylene Triamine Penta (Methylene phosphonate) | | | | | |
|---|---|---|---|---|---|---|---|---|---|---|---|---|
| | 1 Hr. | | 2 Hr. | | 4 Hr. | | 1 Hr. | | 2 Hr. | | 4 Hr. | |
| Organ | $^{113m}$In | $^{85}$Sr | $^{113m}$In | $^{85}$Sr | $^{113m}$In | $^{85}$Sr | $^{113m}$In | $^{85}$Sr | $^{113m}$In | $^{85}$Sr | $^{113m}$In | $^{85}$Sr |
| Kidney | 1.62 | 0.681 | 1.41 | 0.560 | 0.812 | 0.332 | 2.43 | 0.860 | 1.09 | 0.643 | 1.03 | 0.401 |
| Marrow | 0.965 | 0.745 | 0.645 | 0.537 | 0.877 | 0.641 | 0.710 | 1.10 | 0.340 | 0.477 | 0.432 | 0.616 |
| Urine | 34.1 | 3.43 | 48.2 | 14.9 | 49.1 | 30.7 | 31.2 | 5.58 | 65.7 | 17.1 | 69.9 | 19.7 |
| One Femur | 0.94 | 1.08 | 1.04 | 1.37 | 1.25 | 1.53 | 0.782 | 1.13 | 0.648 | 1.27 | 0.621 | 1.40 |
| One Tibia | 0.725 | 0.836 | 0.814 | 1.12 | 0.951 | 1.17 | 0.641 | 0.918 | 0.519 | 1.03 | 0.471 | 1.06 |
| | % Dose/1% Bodyweight | | | | | | | | | | | |
| Blood | 1.80 | 1.52 | 1.21 | 0.941 | 0.696 | 0.589 | 1.23 | 1.70 | 0.555 | 0.952 | 0.441 | 0.723 |
| Liver | 0.673 | 0.711 | 0.306 | 0.416 | 0.216 | 0.267 | 0.276 | 0.665 | 0.173 | 0.405 | 0.184 | 0.335 |
| Muscle | 0.157 | 0.309 | 0.111 | 0.231 | 0.076 | 0.151 | 0.107 | 0.305 | 0.044 | 0.223 | 0.044 | 0.201 |
| Kidney | 3.85 | 1.60 | 2.68 | 1.08 | 2.17 | 0.900 | 5.62 | 1.96 | 2.40 | 1.38 | 2.28 | 0.886 |
| Marrow | 0.438 | 0.339 | 0.305 | 0.244 | 0.399 | 0.291 | 0.322 | 0.500 | 0.154 | 0.217 | 0.196 | 0.279 |
| Femur | 3.73 | 4.32 | 4.50 | 5.95 | 5.45 | 6.57 | 3.57 | 5.17 | 3.07 | 6.00 | 2.97 | 6.65 |
| Tibia | 3.29 | 3.82 | 4.12 | 5.69 | 5.16 | 6.09 | 3.39 | 4.86 | 2.92 | 5.76 | 2.76 | 6.12 |
| Pelvis | 6.71 | 6.09 | 8.21 | 8.06 | 8.86 | 6.75 | 7.15 | 8.41 | 6.15 | 8.34 | 6.37 | 8.75 |
| Spine | 4.96 | 5.36 | 5.87 | 7.11 | 6.31 | 7.04 | 4.80 | 7.11 | 4.59 | 7.61 | 5.16 | 9.13 |
| Average Bone | 5.06 | 5.17 | 6.12 | 6.99 | 6.82 | 6.70 | 5.14 | 6.83 | 4.58 | 7.27 | 4.79 | 8.10 |
| | Ratios | | | | | | | | | | | |
| Bone/Blood | 2.81 | 3.40 | 5.05 | 7.43 | 9.80 | 11.37 | 4.17 | 4.01 | 8.25 | 7.63 | 10.8 | 11.2 |
| Bone/Marrow | 11.55 | 15.25 | 20.10 | 28.65 | 17.1 | 23.02 | 15.9 | 13.6 | 29.7 | 33.5 | 24.4 | 29.0 |
| Bone/Muscle | 32.2 | 16.7 | 55 | 30 | 90 | 44 | 48.0 | 22.3 | 104 | 32.6 | 108 | 40.2 |

For each time interval 3 animals were used and average values are set forth. The average bone concentrations expressed as % dose/1% body weight:

% dose/1% body weight $$= \frac{\text{percent injected dose in sample or organ}}{\text{body weight}} \times \frac{\text{wt of sample or organ}}{1} \times 100$$

$$= (\text{percent dose/gm}) \times \frac{\text{body wt. in gm}}{100}$$

are the mean of the concentrations in bone samples from femur, tibia, spine and pelvis. This value was calculated for individual rabbits and the mean value of these averages are shown. The values for ratios were calculated in a similar manner.

It should be noted that the phosphorous atom in the phosphonate complexes of the compounds of the invention is connected to the nitrogen through a methylene group as compared to the P-O-P bond in the pyrophosphate complexes known as bone-seeking agents. The linkages also differs from the P-C-P linkage in the diphosphonates and the P-N-P structure in the iminodiphosphonate complexes which are also known as bone-seeking agents in the imaging art.

Referring to the drawing, the distinct difference in delineation of the vertebrae, ribs between Indium 113-m and Indium 111 for the same chelating agent is due mainly to the better imaging characteristics of the lower energy gammas of Indium 111. In the figure, the large accumulation of activity seen in the pelvic area of the rabbits is due to urinary excretion of these complexes.

With respect to Table 1, Strontium 85 was employed as a biological standard to compare the uptake in various organs of individual groups of animals. In quantifying the bone uptake, it is necessary to compare more than merely the indium concentration from one group to another. In addition, the ratios of indium to strontium from each group should be compared because of the individual variation of bone uptake in animals.

Alternatively, the phosphonic acids could be kept in a freeze-dried form together with suitable buffers, (e.g. phosphate, bicarbonate) and the composition made by merely mixing the required dosage of Indium-113m or Indium-111 solutions in 0.05 N HCl. The final pH can be adjusted to between 7.0 and 8.0 by a suitable admixture of buffer and the above phosphonic acid or their salts.

25 mg. of EDTMP with 140 mg. of sodium or potassium monohydrogen phosphate in a freeze-dried form is suitable for preparing the complex with 2 to 5 ml of 0.05N HCl solution containing any amount of carrier-free $^{113m}$In or $^{111}$In (e.g., 25–2000 mCi). Instead of monohydrogen phosphate, bicarbonate can also be used.

What is claimed is:

1. A bone-seeking skeletal imaging agent comprising a complex of Indium-113m or Indium-111 with ethylene diamine tetra (methylene phosphonic) acid, diethylene triamine penta(methylene phosphonic) acid, or a salt thereof with a pharmaceutically acceptable cation.

2. A bone-seeking agent according to claim 1 comprising an Indium-113m-ethylene diamine tetra (methylene phosphonate) complex.

3. A bone-seeking agent according to claim 1 comprising an Indium-113m-diethylene triamine penta(methylene phosphonate) complex.

4. A bone-seeking agent according to claim 1 comprising an Indium-111-ethylene diamine tetra(methylene phosphonate) complex.

5. A bone-seeking agent according to claim 1 comprising an Indium-111-diethylene triamine penta(methylene phosphonate) complex.

6. A bone-seeking composition comprising a solution adapted for intravenous administration containing a complex according to claim 1.

7. The composition of claim 6 in unit dosage form containing 5–20 mCi of radioactivity.

8. A method of preparing the skeletal imaging agent of claim 1 comprising admixing in aqueous solution Indium-113m or Indium-111 and ethylene diamine tetra (methylene phosphonic) acid, diethylene triamine penta(methylene phosphonic) acid or a salt thereof with a pharmaceutically acceptable cation.

9. The method of claim 8 wherein said cation is sodium, potassium or ammonium.

10. A method of skeletal-imaging which includes the intravenous administration of a solution adapted for intravenous administration containing a complex according to claim 1.

11. A method of skeletal-imaging which includes the intravenous administration of a solution adapted for intravenous administration containing a complex according to claim 2.

12. A method of skeletal-imaging which includes the intravenous administration of a solution adapted for intravenous administration containing a complex according to claim 3.

13. A method of skeletal-imaging which includes the intravenous administration of a solution adapted for intravenous administration containing a complex according to claim 4.

14. A method of skeletal-imaging which includes the intravenous administration of a solution adapted for intravenous administration containing a complex according to claim 5.

* * * * *